United States Patent
Mu et al.

(10) Patent No.: US 11,874,248 B2
(45) Date of Patent: Jan. 16, 2024

(54) ELECTROCHEMICAL GAS SENSOR ASSEMBLY

(71) Applicant: RAE Systems, Inc., Sunnyvale, CA (US)

(72) Inventors: Qinghui Mu, Shanghai (CN); Jianglin Jian, Shanghai (CN); Feng Liang, Shanghai (CN); Ling Liu, Shanghai (CN); Na Wei, Shanghai (CN)

(73) Assignee: RAE SYSTEMS, INC., Sunnyvale, CA (US)

( * ) Notice: Subject to any disclaimer, the term of this patent is extended or adjusted under 35 U.S.C. 154(b) by 534 days.

(21) Appl. No.: 17/247,125

(22) Filed: Dec. 1, 2020

(65) Prior Publication Data

US 2021/0172901 A1 Jun. 10, 2021

(30) Foreign Application Priority Data

Dec. 5, 2019 (CN) .......................... 201911257074.2

(51) Int. Cl.
*G01N 27/404* (2006.01)
*B01D 53/02* (2006.01)

(52) U.S. Cl.
CPC ......... *G01N 27/4045* (2013.01); *B01D 53/02* (2013.01); *B01D 2253/102* (2013.01); *B01D 2257/708* (2013.01); *B01D 2259/45* (2013.01)

(58) Field of Classification Search
None
See application file for complete search history.

(56) References Cited

U.S. PATENT DOCUMENTS

| 2017/0016847 A1 | 1/2017 | Saffell et al. |
| 2019/0025246 A1 | 1/2019 | Liu et al. |

FOREIGN PATENT DOCUMENTS

| CN | 101571506 B | 2/2016 |
| EP | 0127387 A2 | 12/1984 |
| WO | 2005/015195 A1 | 2/2005 |
| WO | 2011/053721 A1 | 5/2011 |
| WO | 2015/200755 A1 | 12/2015 |

OTHER PUBLICATIONS

Intention to grant dated Apr. 14, 2023 for EP Application No. 20211117, 9 page(s).
Extended European Search Report issued in European Application No. 20211117.5 dated Apr. 26, 2021, 9 pages.
(Continued)

*Primary Examiner* — J. Christopher Ball
(74) *Attorney, Agent, or Firm* — Alston & Bird LLP (57) ABSTRACT

Various example embodiments described herein relate to a sensor assembly. The sensor assembly includes a first sensor cover and a second sensor cover. The first sensor cover is disposed on a first end of the sensor assembly and the second sensor cover is disposed on a second end of the sensor assembly. The first sensor cover defines a first capillary and the second sensor cover defines a second capillary therethrough. The sensor assembly further includes a first sensing unit, a second sensing unit, and a filter. The first sensing unit and the second sensing unit are disposed between the first sensor cover and the second sensor cover. In some example embodiments, the filter is reactive to a target gas and thereby prevents an inflow of the target gas through the second capillary into the sensor assembly.

20 Claims, 5 Drawing Sheets

(56) References Cited

OTHER PUBLICATIONS

Application Note MEM1 Electrochemical Gas Sensor. MEM1 Appl. Note Rev. Sep. 2020 (19 pages). www.membrapor.ch/sheet/Application_Note_MEM1_pdf. Accessed Mar. 2, 2021.
Decision to grant a European patent dated Aug. 4, 2023 for EP Application No. 20211117, 2 page(s).
European search report dated Nov. 15, 2023 for EP Application No. 23191803, 8 page(s).

ELECTROCHEMICAL GAS SENSOR ASSEMBLY

CROSS-REFERENCE TO RELATED APPLICATIONS

This application claims priority to and the benefit of Chinese Patent Application No. 201911257074.2 filed Dec. 5, 2019, each of which is incorporated herein by reference in its entirety.

TECHNOLOGICAL FIELD

The present disclosure relates generally to an electrochemical gas sensor and more particularly to a structure and assembly of the electrochemical gas sensor, and the systems and apparatuses associated therewith.

BACKGROUND

Gas monitoring systems are commonly installed in workplaces and other premises, to monitor concentration of various gases present in a working environment. Such gas monitoring systems are often referred to as gas analyzers, gas detectors, gas sensors, and/or the like. One such type of gas sensor is an electrochemical gas sensor (EGS). Electrochemical gas sensors (EGS) can be used to detect various types of gases, such as oxygen as well as toxic gases including, but not limited to, Carbon Monoxide (CO), Sulphur Dioxide ($SO_2$), Hydrogen Sulfide ($H_2S$), Formaldehyde ($CH_2O$), and/or the like. Existing electrochemical gas sensors are often used for the detection of the gas but are often prone to providing imprecise sensor readings relating to any changes in environmental parameters, such as temperature and humidity, to which a sensor assembly and its associated components are exposed. Accordingly, there is an ongoing desire in the industry for electrochemical gas sensors that are more robust, i.e., sensors that can avoid many pitfalls of existing electrochemical sensors.

SUMMARY

Various example embodiments described herein relate to a sensor assembly (also referred to as "EGS assembly"). The sensor assembly includes a first sensor cover disposed on a first end of the sensor assembly and a second sensor cover disposed on a second end of the sensor assembly. The first sensor cover defines a first capillary therethrough and the second sensor cover defines a second capillary therethrough. The sensor assembly further includes a first sensing unit and a second sensing unit positioned between the first sensor cover and the second sensor cover.

In one exemplary embodiment, the first sensor cover is disposed on a first end of the EGS assembly. Further, the first sensor cover defines a first capillary. In some example embodiments, the second sensor cover is disposed on a second end of the EGS assembly and defines a second capillary therethrough. Furthermore, the EGS assembly includes a sensing element positioned between the first sensor cover and the second sensor cover.

In accordance with another example embodiment, the first sensing unit includes at least a sensing electrode, a reference electrode, and a counter electrode. The second sensing unit includes an auxiliary electrode. In accordance with another exemplary embodiment, the sensing electrode can be positioned on the first end of the EGS assembly. Further, the auxiliary electrode can be positioned on the second end of the EGS assembly. The counter electrode and the reference electrode are positioned between the sensing electrode and the auxiliary electrode.

In some example embodiments, the sensor assembly also includes a filter. The filter is defined by a material which is reactive to a target gas. Further, the filter can be positioned on the second capillary to prevent an inflow of the target gas through the second capillary. In this regard, the passage defined by the first capillary allows the target gas to pass therethrough. However, the filter positioned on the second capillary prevents the gas to pass therethrough.

In accordance with various embodiments described herein, the filter includes at least one of a membrane or a chemical substance. Further, in another exemplary embodiment, the membrane can be a porous PTFE membrane or a glass fiber membrane. In accordance with one exemplary embodiment, the chemical substance corresponds to potassium permanganate that can filter the target gas, or a mixture of the chemical substance with the porous PTFE membrane or PTFE powder. In this regard, in some examples, an activated carbon filter can be used as the membrane for filtering the target gas.

In accordance with some exemplary embodiments, a printed circuit board (PCB) can be coupled to the EGS assembly. The printed circuit board can be configured to determine a first current and a second current. The first current is based on a first reaction between the target gas and the first sensing unit in the presence of at least one environmental parameter. The second current is based on a second reaction at the second sensing unit. In this regard, the first current corresponds to an amount of the target gas at the first sensing unit and the second current corresponds to a magnitude of the at least one environmental parameter at the second sensing unit.

In accordance with some example embodiments, the printed circuit board can be further configured to determine a differential current. The differential current depends on the first current and the second current. To this end, the differential current can correspond to an amount of noise level based on the magnitude of the at least one environmental parameter. In some examples, the at least one environmental parameter includes at least one of a temperature value or a humidity value. The temperature and humidity values correspond to relative temperature and humidity values which are induced within the EGS assembly due to ambient conditions.

In accordance with another example embodiment, another sensor assembly is described. The sensor assembly includes a first sensing unit, a second sensing unit, a first sensor cover, and a second sensor cover. Further, the first sensor cover defines a first capillary and the second sensor cover defines a second capillary. In some examples, the first capillary can be laminated with a chemical substance which acts as a filter or a barrier for the target gas. The filter can be adapted to prevent an inflow of a target gas through the first capillary based on a reaction between the filter and the target gas. In another exemplary embodiment of the invention, the filter can be adapted to convert the target gas from one form to another form.

In one exemplary embodiment of the invention, the second capillary permits the inflow of the target gas therethrough. The target gas reaches the sensing electrode and generates sensing current based on a reaction of the target gas with the sensing electrode.

In another exemplary embodiment, the second sensing unit can be coupled to the first sensor cover and the first sensing unit can be coupled to the second sensor cover.

According to an exemplary embodiment, the sensing electrode can be positioned on a first end of the sensor assembly and the auxiliary electrode can be positioned on a second end of the sensor assembly.

In accordance with one exemplary embodiment, another sensor assembly is described. The sensor assembly includes a housing, a second sensor cover, a first sensing unit, a second sensing unit, and a filter. Further, the filter is defined by a material which is reactive to the target gas. The second sensor cover can be positioned on a second end of the housing. Further, the housing includes a first sensor cover. In some example embodiments, the first sensor cover can be positioned on a first end of the housing.

Furthermore, in some examples, the first sensing unit and the second sensing unit are positioned between the first sensor cover and the second sensor cover. In this regard, in some example embodiments, the first sensor cover defines a first capillary and the second sensor cover defines a second capillary, respectively. The first capillary is configured to allow a target gas to pass therethrough. The target gas after passing through the first capillary reacts with the sensing electrode of the first sensing unit. The reaction between the target gas and the first sensing unit results in generation of a sensing current. The sensing current corresponds to an amount of the target gas. However, the filter positioned to be in a fluidic communication with the second capillary prevents the inflow of the target gas through the second capillary.

In some example embodiments, the first sensing unit includes a sensing electrode, a reference electrode, and a counter electrode, and the second sensing unit includes an auxiliary electrode. Further, in one exemplary embodiment, the sensing electrode can be coupled with the first capillary. The auxiliary electrode can be coupled with the second capillary within the housing. The reference electrode and the counter electrode can be positioned between the sensing electrode and the auxiliary electrode.

According to some example embodiments, the sensor assembly further comprises a printed circuit board configured to determine a first current based on a first reaction, in the presence of at least one environmental parameter. The printed circuit board is further configured to determine a second current based on a second reaction at the second sensing unit. The first current corresponds to an amount of the target gas at the first sensing unit and the second current corresponds to a magnitude of the at least one environmental parameter.

In some example embodiments, the printed circuit board is further configured to determine a differential current based on the first current and the second current. The differential current corresponds to an amount of noise level based on the magnitude of the at least one environmental parameter.

According to some example embodiments, a first dimension of the first capillary can be the same as a second dimension of the second capillary.

In some exemplary embodiments, a structure to build a four-electrode EGS is described. The four-electrode EGS can be adapted to remove the ambient environmental effects. The auxiliary electrode can be designed to detect current generated due to change(s) in environmental parameters.

In one of the exemplary embodiments, the sensing electrode and the auxiliary electrode are placed separately at each end of the EGS assembly (e.g., any sensor cylinder), with two diffusion capillaries located on the sensor top and bottom, respectively. The sensing electrode is exposed to the target gas via the first capillary. In another embodiment, the auxiliary electrode is exposed to the external environmental conditions through the second capillary. However, the target gas cannot pass through the second capillary due to the presence of the filter on the second capillary. The sensing electrode and the auxiliary electrode are exposed to the same environmental conditions.

In one of the exemplary embodiments, the filter is defined by a material, a membrane, or a powder filter which is reactive to the target gas. Further, the filter is positioned on the second capillary. The membrane or chemical powder or an activated carbon filter can be used to protect the auxiliary electrode from the exposure of the target gas. This type of sensor can be more robust and stable while monitoring environmental effects and target gas simultaneously. Therefore, the EGS assembly can be more accurate in responding to the change in gas concentration based on change(s) in environmental parameters.

The above summary is provided merely for purposes of providing an overview of one or more exemplary embodiments described herein to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which are further explained within the following detailed description and its accompanying drawings.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In accordance with some example embodiments, the EGS assembly as described herein can comprise electrodes. The "electrodes" may comprise graphite and/or one or more metals such as copper, silver, gold, nickel, palladium, platinum, ruthenium, iridium, other suitable metals, oxides of these metals, or combinations thereof. The materials used for the individual electrodes may be the same or different. In addition, a catalyst can be used with the electrode to accelerate the rate of a chemical reaction. In this regard, the catalyst can include a pure metal powder, a metal powder combined with carbon, a metal powder supported on an electrically conductive medium such as carbon, a combination of two or more metal powders either as a blend or as an alloy, or other suitable configurations.

The electrodes may include a reactive material suitable for carrying out a desired reaction. For example, the electrodes can be formed of a mixture of electrically conductive catalyst particles in a binder such as polytetrafluoroethylene (PTFE).

The "separator" as described herein may comprise a nonwoven porous material (e.g., a porous felt member), a woven porous material, a porous polymer (e.g., an open cell foam, a solid porous plastic, etc.), or the like, and can be generally chemically inert with respect to the electrolyte and the materials forming the electrodes. In an embodiment, the separator may be formed from various materials that are substantially chemically inert to the electrolyte including, but not limited to, glass (e.g., a glass mat), polymer (plastic discs), ceramics, or the like.

The "electrolyte" as described herein may comprise any aqueous electrolyte such as a solution of a salt, an acid, a base, or the like, depending on the target gas of interest. According to various example embodiments described herein, the electrolyte may comprise a hygroscopic acid such as sulfuric acid for use in an oxygen sensor. Other target gases may use the same or different electrolyte compositions. In addition to aqueous based electrolytes, ion liquid electrolytes may also be used to detect certain gases.

Electrochemical gas sensors are typically utilized for sensing at ppm-level detection. Some example embodiments described herein relate to an electrochemical gas sensor with increased sensitivity which can be used for sensing at ppb-level detection. In some examples, three electrodes can be used in a gas sensor to detect a target gas (e.g. formaldehyde) in a home environment. Typically, in operation, a baseline of the electrochemical gas sensor is often affected by ambient environmental parameters (or meteorological parameters) such as humidity or temperature. Accordingly, in such cases, an output current of the electrochemical gas sensor changes rapidly with changes in humidity or temperature within sensor assembly. Moreover, an effect of temperature and humidity lasts for a long duration of time (e.g. several hours). Therefore, some electrochemical gas sensors described herein may comprise a fourth electrode (e.g., an auxiliary electrode) to measure the effect due to humidity and/or temperature. To this end, the fourth electrode, also known as auxiliary electrode (AE), is adapted to remove the ambient effects of environmental parameters, or to improve the sensor selectivity. In some examples, the auxiliary electrode can usually be located below the sensing electrode (SE) with one diffusion capillary.

Typically, electrochemical gas sensors (EGS) are used for the detection of a target gas in a gas concentration inflowed into the electrochemical gas sensor. The target gas is detected based on a chemical reaction between the target gas and the sensing electrode, at the sensing electrode. In this regard, as a result of the chemical reaction, electric current is generated depending on a type and amount of the target gas present in the gas concentration. The EGS generally operate based on a 'redox' reaction that occurs inside the EGS, e.g., when a target gas is diffused inside an assembly of the EGS. In this regard, during a redox reaction inside the EGS, a metal cathode in a first part of the EGS may chemically reduce oxygen from the target gas while a balancing reaction oxidizes an anode in the second part of the EGS. To this extent, in the EGS, the cathode and the anode can be coupled, operably coupled, fluidically coupled, and/or chemically coupled using an ionically conducting electrolyte. In this regard, a flow of current due to the redox reaction at the metal cathode and the anode provides a measurement of a concentration of the target gas detected by the EGS.

To this end, generally, components of the EGS are often exposed to environmental parameters and/or conditions (e.g., pressure differential or temperature) that affect an operating performance of the EGS. For instance, in some cases, presence of environmental parameters such as pressure differential and humidity effects measurement of the target gas by the EGS. In this regard, such parameters often cause generation of noise signals and fluctuations in a signal sensed by the sensing electrode of the EGS corresponding to the detection of the target gas. Thus, the noise signals and fluctuations in output current, due to presence or variation in environmental parameters, result in a change in actual current value that would have been reported due to presence of the target gas, thereby effecting sensor output. Typically, in operation of the EGS, an effect of such environmental parameters and conditions to which components of the sensor assembly are exposed lasts for a long time and the EGS does not regain their original state quickly. Thus, it is desired to minimize noise from a sensed signal value, in order to determine whether the sensed signal accurately represents a concentration of the target gas in a gas concentration.

Various exemplary embodiments described herein relate to an electrochemical gas sensor (EGS). The EGS described herein provides an improved sensor assembly. The improved sensor assembly can be used for the accurate determination of a target gas, irrespective of interference in sensing output. The cause of interference can be due to environmental parameters within the EGS assembly to which components of the EGS are exposed, but is not limited to these parameters only.

Further, in accordance with some example embodiments, the environmental parameters include change in temperature and humidity but are not limited to these only. Further, the change in temperature shifts the equilibrium of the reaction from stable to an unstable state. The shift of the equilibrium depends on the temperature coefficient of the electrodes. In addition, the redox reaction is controlled by viscosity of the electrolyte and viscosity is adapted to change based on a change in temperature. Furthermore, temperature or heat can be in any form, such as IR radiation, but are not limited to this only. The increase in heat or temperature accelerates the rate of redox reaction and the sensed current fluctuates from the actual values.

Further, in accordance with some example embodiments, the effect of humidity is also similar to the effect of temperature. The rate of redox reaction increases with increase in humidity level due to an increase in ion concentration. The level of humidity and heat affects the current values at the sensing electrode and the auxiliary electrode simultaneously.

Figure 1:
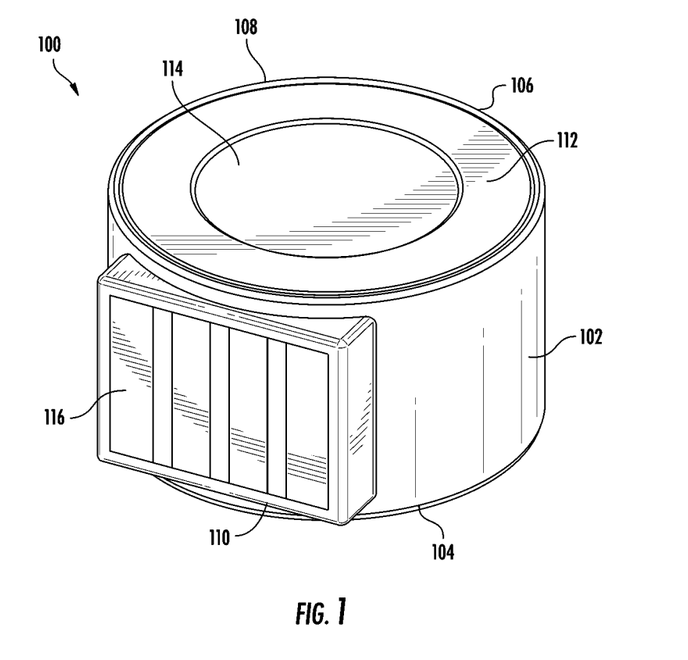
FIG. 1 illustrates a perspective view of an electrochemical gas sensor, in accordance with some example embodiments described herein.

FIG. 1 illustrates a perspective view of an electrochemical gas sensor (EGS) 100, in accordance with some exemplary embodiments described herein. The EGS 100 illustrated herein represents an external structure defined by a sensor body 102 (also referred to hereinafter throughout the description interchangeably as a sensor assembly for purposes of brevity). Illustratively, the sensor body 102 can be defined between a first end 104 and a second end 106. In this regard, the first end 104 corresponds to an end that defines a top surface 108 of the sensor body 102. Similarly, the second end 106 corresponds to an end of the sensor body 102 that defines a bottom surface 110 of the sensor body 102.

The EGS 100 further includes a sensor cover 112 and a dust cover 114. In accordance with some example embodiments described herein, the sensor cover 112 has a first surface and a second surface and defines a capillary therethrough (not shown herein). In some example embodiments, the sensor cover 112 can be of a shape, such as, but not limited to, a cylindrical cap shape or a disc shape, and/or the like that can be positioned on the top surface 108 including the second end 106 of the sensor body 102. Further, in accordance with some example embodiments, the dust cover 114 can be positioned over the sensor cover 112. Positioning of the dust cover 114 over the sensor cover 112 prevents an inflow of dust particles therethrough into the sensor assembly (i.e. the sensor body 102).

According to some example embodiments, the EGS 100 further includes a printed circuit board (PCB) 116 that can be coupled with the sensor body 102. In addition to the above-mentioned components, in some example embodiments, the EGS 100 can include one or more sensing elements (e.g., a sensing die), and a filter, details of which are described in reference to FIGS. 2-5. In accordance with various example embodiments, the EGS 100 can be used for sensing a target gas from a gas concentration.

In some examples, the EGS 100 can be used in some industries where it is critical to measure a target gas, regardless of environmental fluctuations such as temperature and humidity to which the sensor assembly is exposed. To this end, in accordance with various example embodiments described herein, the EGS 100 can be adapted to determine the target gas by removing a contribution of a noise signal from a sensed signal. In this regard, the noise signal can be a signal that accounts for noise due to a change in environmental parameters experienced by the EGS 100 and that causes errors in sensor reading.

Figure 2:
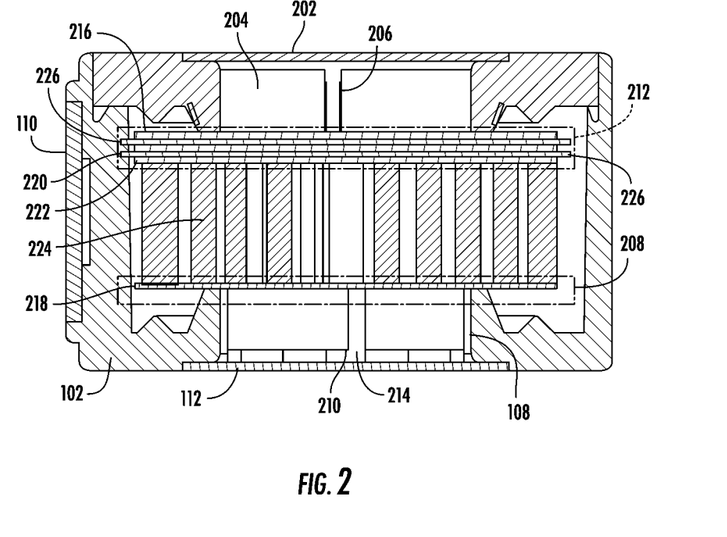
FIG. 2 illustrates a sectional view of an electrochemical gas sensor take through the midpoint of the sensor and extending through a printed circuit board, in accordance with some example embodiments described herein.

FIG. 2 illustrates a sectional view of the electrochemical gas sensor (EGS) 100, in accordance with some example embodiments described herein. The sectional view of EGS 100, illustrated in FIG. 2, represents an internal structure and arrangement of components of the EGS 100. In this regard, starting from a top end, according to some example embodiments, the EGS 100 includes a dust cover 202 that can have a shape of a disc and can be positioned over a sensor cover 204. The dust cover 202 may comprise a dust cap, a sealing jacket or a cover encompassing the sensor cover 204. In some example embodiments, the dust cover 202 can be made of rubber, nylon, polyamide, or any other material. In this regard, in some example embodiments, the material of the dust cover 202 can be selected from a permeable membrane or a semi permeable membrane which prevents the passage of dust particles but allows the passage of a target gas therethrough into the sensor assembly.

Further, in some example embodiments, the EGS 100 further includes a first sensing unit 212. Illustratively, the first sensing unit 212 is fluidically coupled to the sensor cover 204. In some example embodiments, the sensor cover 204 has a top surface and a bottom surface. The sensor cover 204 can further define a capillary 206 therethrough between the top surface and the bottom surface. Further, in some example embodiments, the capillary 206 extends between the first sensing unit 212 and the sensor body 102.

In some example embodiments, the first sensing unit 212 includes a sensing electrode 216, a reference electrode 220, and a counter electrode 222. In some example embodiments, the sensing electrode 216, the reference electrode 220, and the counter electrode 222 can be any solid electric conductor which are adapted to carry electric current into non-metallic solids, liquids, gases, plasmas, or vacuums, but are not limited to these only.

According to some example embodiments, the EGS 100 may comprise sensing unit in two halves, where a pair of electrodes including the sensing electrode 216 and the reference electrode 220 defines a first half of the EGS 100 and another pair of electrodes including the counter electrode 222 and the reference electrode 220 defines a second half of the EGS 100. In this regard, the sensing electrode 216 provides a current as a result of redox reaction at the sensing electrode 216. Further, in such examples, depending on the type of target gas, the sensing electrode 216 and the counter electrode 222 can act as an anode terminal or cathode terminal, respectively.

As illustrated, the EGS 100 includes one or more separators (e.g. a separator 226) that can be positioned between the electrodes to separate the sensing electrode 216, the reference electrode 220, and the counter electrode 222. In this regard, in one exemplary embodiment, the separator 226 can include an aperture that can be dimensioned to receive the first sensing unit 212. Further, in some example embodiments, the separator 226 can be operable to isolate the sensing electrode 216 with components below the separator 226 in the EGS 100 assembly.

In some embodiments, the EGS 100 can further include one or more separators 226. The separators 226 may be dimensioned and configured to provide a crossover path to the sensing electrode 216, the reference electrode 220, and the counter electrode 222 inside the EGS 100. In this aspect, the separators 226 may also provide an ionic pathway for an electrochemical pump action to occur inside the EGS 100.

As illustrated, the EGS 100 further includes a second sensing unit 208. Further, in some example embodiments, the second sensing unit 208 can be fluidically coupled with the sensor cover 112.

In another exemplary embodiment, the second sensing unit 208 can include an auxiliary electrode 218. In this regard, as illustrated, in some example embodiments, a first surface of the auxiliary electrode 218 can be coupled with a first surface of the sensor cover 112. Further, the second surface of the auxiliary electrode 218 can be immersed in an electrolyte. In accordance with some example embodiments described herein, physical and chemical properties of the auxiliary electrode 218 can be similar to that of the sensing electrode 216. Further, in one exemplary embodiment, the sensitivity of the auxiliary electrode 218 can be increased by using a layer of a catalyst, which is reactive to a change in humidity and temperature, on the auxiliary electrode 218.

In some example embodiments, the sensor cover 112 has a top surface and a bottom surface defining a capillary 210 therethrough. In this regard, the bottom surface of the sensor cover 112 is positioned on the first sensing unit 212 and the top surface of the sensor cover 112 is coupled with a filter 214. Further, the capillary 206 extends between an outer surface of the sensor body 102 and the first sensing unit 212. In a similar manner, the capillary 210 extends in between the filter 214 and the second sensing unit 208. In accordance with various exemplary embodiments described herein, the capillary 206 can act as a gas inlet such that air mixture including a target gas can inflow into the EGS 100 via the capillary 206.

In some example embodiments, the filter 214 includes a material which is reactive to the target gas. The filter 214 is adapted to prevent the ingress of the target gas through the second capillary 210.

In another exemplary embodiment, the EGS 100 further includes the printed circuit board (PCB) 116, a wick 224, and electric wires (not shown explicitly). Further, the sensor assembly of the EGS 100 can be further connected to a substrate of the PCB 116.

In accordance with various example embodiments described herein, the target gas may flow through the first capillary 206 and reach the first sensing unit 212. At the first sensing unit 212, the target gas reacts with the sensing electrode 216 in the presence of various environmental parameters. The environmental parameters include, for example, temperature and humidity, but are not limited to these only. The environmental parameters may comprise the relative temperature (i.e., an amount of heat level), and relative humidity values present in the vicinity of the EGS 100.

In some embodiments, the wick 224 can be adapted to draw an electrolyte by capillary action, as desired, through a stack of the various components of the EGS 100. In this aspect, the wick 224 may capture the electrolyte from a body cavity of the EGS 100 to maintain a liquid level throughout at least a portion of the stack of components of the EGS 100. Further, the wick 224 may provide an ionic pathway for electrochemical pump action to occur inside the EGS 100. The wick 224 may also provide a wetted interface for the counter electrode 222 and the auxiliary electrode 218 and may prevent or partially prevent the target gas to pass therethrough.

Figure 3:
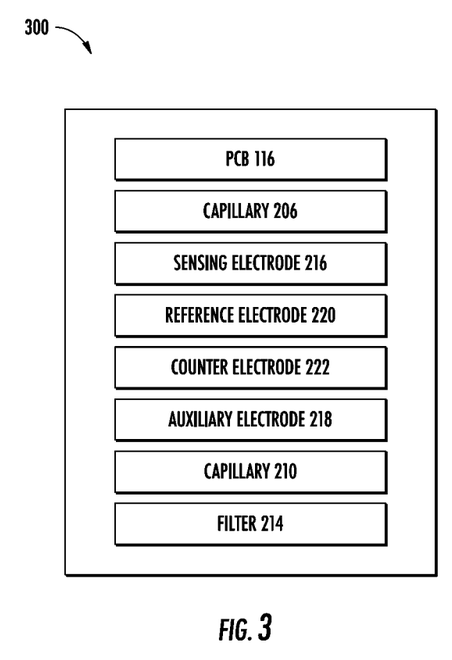
FIG. 3 schematically depicts a block diagram representing various components of an electrochemical gas sensor, in accordance with some example embodiments described herein.

FIG. 3 schematically depicts a block diagram representing various components of a system of an electrochemical gas sensor (EGS) 300 (for example, the EGS 100 as described in FIGS. 1 and 2 respectively). Illustratively, the EGS 300 can include components, for example, but not limited to, the first sensing electrode 216, the reference electrode 220, the counter electrode 222, the auxiliary electrode 218, the first sensor cover 204, the sensor cover 112, the PCB 116, the first capillary 206, the second capillary 210, and the filter 214. In accordance with some exemplary embodiments, the EGS 300 is operable to detect a target gas based on an electrochemical reaction at the sensing electrode 216 of the EGS 300.

In accordance with some exemplary embodiments described herein, the sensing electrode 216 may correspond to an electrode at which at least a portion of a 'redox reaction' takes place upon diffusion of the target gas into the EGS 100, 300. The redox reaction described herein, according to some embodiments, may correspond to an electrochemical reaction involving a reduction reaction at the sensing electrode 216 and a balancing oxidation reaction at the counter electrode 222. The counter electrode 222, in some embodiments, may correspond to an electrode at which current flows upon the reaction at the sensing electrode 216. In addition, the auxiliary electrode 218 may correspond to an electrode at which at least a portion of a redox reaction takes place in the absence of the target gas. In some examples, the current generated at the auxiliary electrode 218 may correspond to a drift in environmental parameters such as relative temperature and relative humidity levels.

In this regard, in accordance with various example embodiments, to balance a reaction at the sensing electrode 216, a counter reaction takes place at the counter electrode 222 and vice versa. For example, in an example situation, if oxidation occurs at the sensing electrode 216, a reduction reaction takes place the counter electrode 222. The reference electrode 220, in some examples, may correspond to an electrode having a stable electrode potential. In this aspect, the reference electrode 220 may provide a measure of potential at sensing electrode 216 without passing current through the reference electrode 220.

Further, the reference electrode 220 may be configured to provide a stable reference potential desired for an electrochemical reaction that may occur inside the EGS 100, 300 during operation of the EGS 100, 300. In this regard, a reaction at the sensing electrode 216 with regards to the reference electrode 220 and the counter electrode 222 results in the sensing current. The sensing current is due to the presence of the target gas at the first sensing unit 212. Further, the sensing current deviates due to a drift in environmental parameters, at least, for example, temperature and humidity.

In one exemplary embodiment, the auxiliary electrode 218 is adapted to determine an auxiliary current in the absence of the target gas. The auxiliary current depends on the amount of change in environmental parameters. The auxiliary current is determined to eliminate the contribution of noise signal from the sensed signal. The noise signal depends on the fluctuations in the environmental parameters such as temperature or humidity.

In one exemplary embodiment, the first capillary 206 and the second capillary 210 have the same dimensions and experience the same environmental conditions. The first capillary 206 and the second capillary 210 with the same dimensions are adapted to be exposed to similar environment conditions. Further, the first capillary 206 allows the gas to pass therethrough and the filter 214 on the second capillary 210 prevents the passage of the target gas therethrough. The sensing current at the first sensing unit 212 corresponds to the target gas and the environmental conditions/parameters. Further, the auxiliary current at the auxiliary electrode 218 is free from the effect of the target gas.

In accordance with various example embodiments described herein, the PCB 116 can be configured to measure a first current based on the reaction of the target gas at the sensing electrode 216. The PCB 116 is further configured to determine a second current based on the reaction due to change in environmental parameters at the auxiliary electrode 218.

In one exemplary embodiment, a circuitry is connected either directly to the EGS 100, 300 or to the PCB 116 and is configured to determine a differential current based on the sensing current and the auxiliary current. In one exemplary embodiment, the differential current results in a subtraction of the auxiliary current from the sensing current or, in other words, the noise or errors signal due to environmental parameters. In one exemplary embodiment, the sensitivity and signal to noise ratio of the EGS 100, 300 can be improved based on the determination of the sensing current and the auxiliary current. In some embodiments, the differential current corresponds to an amount of noise level based on the magnitude of the at least one environmental parameter. The at least one environmental parameter includes at least one of a temperature value or a humidity value, within the sensor assembly.

In some embodiments, the PCB 116 may be further configured to provide a digitized output of the EGS 100, 300, e.g., to a processor, a computing device, a display device, or any other suitable instrument or device for further processing or analysis. In this regard, the digitized output may be related to a target gas monitored by the EGS 100, 300. In some embodiments, the digitized output can include a signal or other transmission form indicative of a concentration of the target gas being monitored. In some embodiments, the digitized output can include a signal or a plurality of signals or other transmission forms indicative of a change in the concentration of the target gas being monitored over time. In some embodiments, the digitized output can be a burst or intermittent stream of batch-wise target gas concentration values over time or a steady stream of real-time or near real-time target gas concentration values.

In some embodiments, the signal or other transmission may include a signal or other transmission indicative of a current or potential between or within the first sensing unit 212. In this regard, the current may flow, e.g., between one or more electrodes (not shown), due to a redox reaction which occurs at the one or more electrodes of the EGS 100, 300. The redox reaction is due to an ingress of the target gas inside the EGS 100, 300. In some embodiments, the PCB 116 may include circuitry for measuring the current and controlling bias on the EGS 100, 300. Additionally, or alternatively, the PCB 116 may include a processing circuitry that is configured to determine the sensing current due to the presence of the target gas at the sensing electrode 216. The processing circuitry is further configured to determine the auxiliary current due to a drift in environmental parameters such as temperature and/or humidity.

According to one exemplary embodiment, the first sensor cover 204 can define the first capillary 206 therethrough and the sensor cover 112 can define the second capillary 210 therethrough. Further, as illustrated, the filter 214 may be positioned on the second capillary 210. The filter 214 is reactive to the target gas and prevents the passage of the target gas therethrough.

Additionally, and/or alternatively, in some example embodiments, the EGS 100, 300 can includes, the dust cover 114, the dust cover 202, the one or more separators 226, the wick 224 and other components not illustrated herein in FIG. 3.

In some embodiments, the EGS 100, 300 can also comprise a catalyst (not shown) that can be used in addition to the sensing electrode 216. In this regard, in some examples, the catalyst can be laminated on the sensing electrode 216 to increase a sensitivity of the sensing electrode 216. Said differently, the catalyst can help in increasing a rate of reaction between the target gas and the sensing electrode 216. According to some example embodiments, a type of catalyst that can be used in the EGS 100, 300 along with the sensing electrode 216 can depend on a target gas to be detected and measured by the EGS 100, 300. In this regard, in some examples, catalysts such as Pt, AG, AU, Ru can be used depending on the type of the target gas to be measured. For instance, in one exemplary embodiment, Pt can be used as a catalyst with the sensing electrode 216 when the target gas is CO. For purposes of brevity, the sensing electrode 216 can also be referred hereinafter interchangeably as working electrode throughout the description.

Figure 4A:
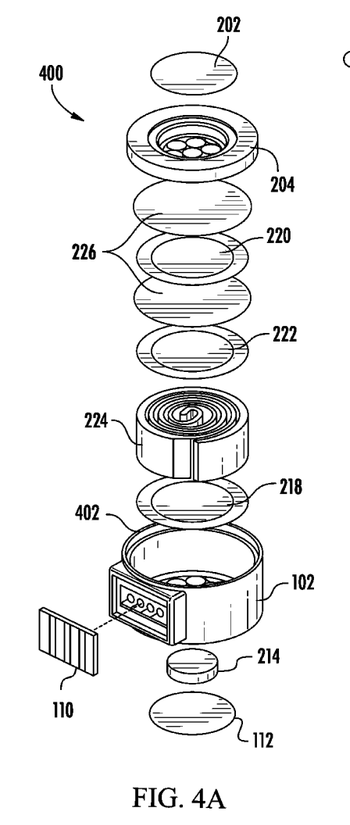
FIG. 4A depicts an exploded top-down view of an electrochemical gas sensor in accordance with some example embodiments described herein.
Figure 4B:
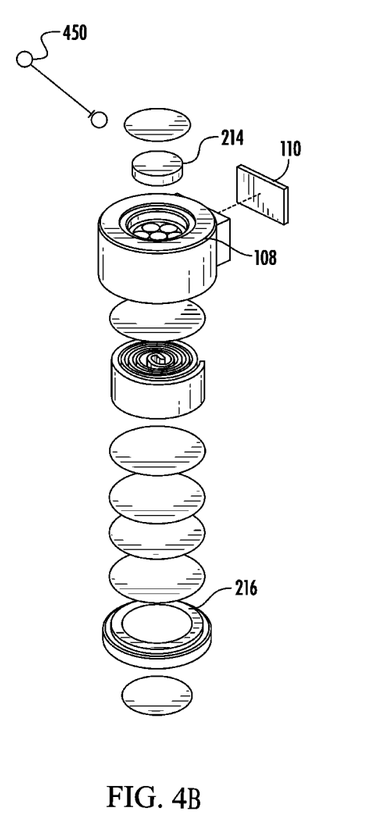
FIG. 4B depicts an exploded bottom-up view of an electrochemical gas sensor, in accordance with some example embodiments described herein.

FIGS. 4A and 4B schematically depicts an exploded top-down view 400 of the electrochemical gas sensor (EGS) 100 and an exploded bottom-up view 450 of the electrochemical gas sensor, in accordance with some example embodiments described herein.

Illustratively, the exploded top-down view 400 of the EGS 100 depicts various components and positioning of the components of the EGS 100. For instance, the exploded top-down view 400 illustrates the dust cover 202 mounted on a first side of the sensor cover 204. The sensor cover 204 is mounted on a first side of the sensing electrode 216. In addition, the sensing electrode 216 is coupled with the reference electrode 220 and the counter electrode 222. The sensing electrode 216 and the reference electrode 220 are separated by the separator 226. In accordance with various exemplary embodiments, a first surface of the auxiliary electrode 218 is mounted on a first surface of the sensor cover 112. Further, the second surface of the auxiliary electrode 218 is immersed within electrolyte. The filter 214 is placed on a second surface of the sensor cover 112. The various components of the EGS 100 may be adapted to be engaged over each other or coupled together to form a sensor assembly 100, e.g., while assembling various components of the EGS 100, described hereinafter. Starting at a lower end, in some embodiments, the sensor body 102 includes the PCB 116.

In accordance with one exemplary embodiment described herein, the sensing electrode 216 can be dimensioned and configured to provide a medium for electrochemical reaction of the target gas that may be diffused inside the EGS 100 through the first capillary 206 of the sensor cover 204. In this aspect, in some example embodiments, the sensing electrode 216 may comprise or be made from a material that provides sufficient activity for reducing the target gas that may contact a surface of an electrocatalyst present on the sensing electrode 216.

In accordance with various example embodiments described herein, on the top surface 108 of the sensor body 102, the auxiliary electrode 218, the wick 224, the counter electrode 222, the reference electrode 220, and the sensor cover 204 are stacked one over the other. The sensing electrode 216 is adapted to generate a first current due to a first chemical reaction at the sensing electrode 216. Similarly, the second sensing unit (i.e., the auxiliary electrode 218) is adapted to generate a second current due to a second chemical reaction at the auxiliary electrode 218.

In accordance with various example embodiments described herein, starting from the top of the exploded bottom-up view 450 of FIG. 4B, the EGS 100 further includes the filter 214, the sensor cover 112 and the sensing electrode 216. The filter 214 is mounted on a cavity defined by the sensor cover 112. The filter 214 is adapted to cover the capillary to prevent the ingress of gas therethrough. In some embodiments, the EGS 100 may not include the PCB 116, but rather the EGS 100 can be operably coupled to an external PCB 116 or other such device such that measurements and/or signals indicative of measurements made by the EGS 100 can be transmitted, stored, and/or displayed on a display device (not shown).

In accordance with various example embodiments described herein, the PCB 116, in accordance with various example embodiments described herein, can be adapted to connect the EGS 100 to external circuitry (not shown). In some embodiments, the EGS 100 can include internal sensor pads (not shown) configured to be coupled to one or more sensor pads (not shown) of the external circuitry in order to couple the EGS 100 and the external circuitry, which may be external to the EGS 100.

In some embodiments, the EGS 100, 300 can include one or more current collecting wires 402 which can be connected to the first and second sensing units 208, 212 and the PCB 116, respectively, as shown in FIG. 4A. In this regard, in some examples, the one or more current collecting wires 402 can be adapted to provide an electrical connection between one or more electrodes of the EGS 100, 300, and further to one or more external contact pads on the PCB 116. For instance, in some embodiments, the one or more current collecting wires 402 may form one or more electrical connections with various components, including but not limited to the sensing electrode 216 via the separator 226, the reference electrode 220, the counter electrode 222, and the auxiliary electrode 218.

Figure 5:
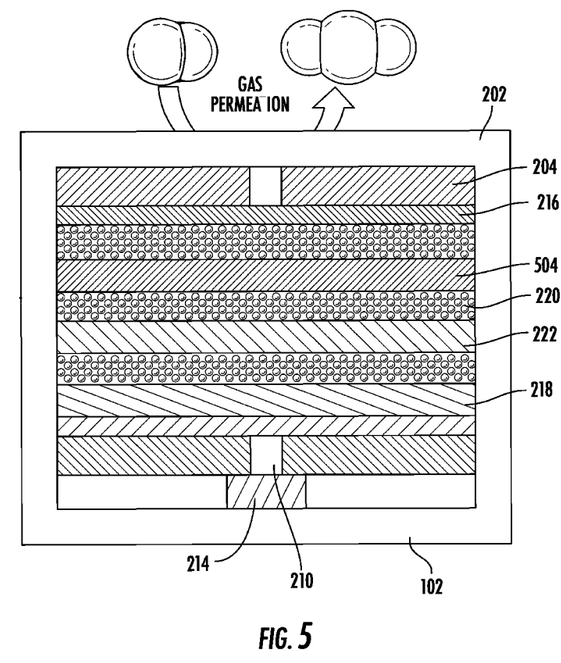
FIG. 5 schematically depicts a sectional view of an electrochemical gas sensor and an operation performed by the electrochemical gas sensor, in accordance with another embodiment described herein.

FIG. 5 schematically depicts a sectional view of the electrochemical gas sensor and operation performed by the electrochemical gas sensor (e.g., EGS 100), in accordance with another embodiment described herein. The structural arrangement of the EGS shown in FIG. 5 is similar to the EGS 100, 300 shown in FIGS. 1-4. Further, the EGS as shown in FIG. 5 includes an electrolyte 504 which is equivalent to the sensor body 102 shown in FIG. 1. Further, the dust cover 114 and the dust cover 202 are adapted to prevent the passage of dust particles therethrough. The filter 214 can be configured to prevent an inflow of the target gas inside the capillary 210 based on a chemical reaction between the filter 214 and the target gas. In one exemplary embodiment of the invention, the filter 214 includes at least one of a membrane, a chemical substance, a mixture of the chemical substance with glass fiber, or a mixture of the chemical substance with PTFE powder. In addition, the membrane comprises an activated carbon filter and the chemical substance includes potassium permanganate to absorb volatile organic compounds (VOC) and content of formaldehyde present in the target gas. The filter 214 prevents the ingress of the target gas due to a reaction between the target gas and the filter 214.

In one exemplary embodiment of the invention, the first capillary 206 may be in fluidic communication with an electrode of an electrochemical cell of the EGS 100. The first capillary 206 may be operable to facilitate an inflow of the target gas inside the EGS 100. The gas inlet provided by the first capillary 206 may extend through a portion of a housing of the EGS 100. During operation of the EGS 100, the target gas may be communicated into or caused to diffuse within the EGS 100 for the purposes of gas concentration measurement and/or monitoring.

In some embodiments, the electrochemical cell can be configured such that the sensing electrode 216 and the counter electrode 222 of the first sensing unit 212, with the wick 224, form a circuit whereby ions can be communicated between the sensing electrode 216 and the counter electrode 222 via the wick 224. The electrons are communicated in an opposite direction between the counter electrode 222 and the sensing electrode 216, creating a measurable current flow which is known as sensing current.

In some embodiments, the sensing electrode 216 may be operably coupled, ionically coupled, electrically coupled, and/or fluidically coupled to the counter electrode 222, e.g., via the wick 224. The EGS 100 may optionally include a reference electrode (not shown). In accordance with various exemplary embodiments described herein, the sensing electrode 216 may also be referred to as a 'working electrode', a 'first electrode', or a 'consuming electrode' and typically refers to the electrode that is configured to be exposed to and to consume at least a portion of the target gas during measurement of the concentration of the target gas.

According to various exemplary embodiments, the EGS 100 or components thereof may be operable to monitor a concentration of the target gas, for example, oxygen or carbon monoxide, based on a redox reaction which takes places when the target gas is diffused inside the EGS 100. To this extent, the electrochemical cell including the sensing electrode 216 may consume the target gas and transmit ions through the wick 224 to the counter electrode 222, and the counter electrode 222 can generate the target gas such that measurement of the concentration of the target gas can be achieved by measuring a flow of current or a potential difference between the sensing electrode 216 and the counter electrode 222 that may be generated due to the electrochemical reaction inside the electrochemical cell.

In some embodiments, the EGS 100 can optionally include the printed circuit board (PCB) 116 comprising a processing circuitry that may be configured to receive a digitized output indicative of values corresponding to the electric current or the voltage generated inside the electrochemical cell of the EGS 100. In this aspect, in accordance with various example embodiments described herein, the processing circuitry may process such values to determine a concentration of the target gas. In another example embodiment, the PCB 116 and the processing circuitry may be located external to the EGS 100.

In this regard, in some examples, one or more electrical contacts of the EGS 100 may connect with the externally located PCB 116 and the associated processing circuitry. In some embodiments, the PCB 116 and the processing circuitry may be located in a remote device which may be connected with the EGS 100, for instance, over a wired or wireless communication network or based on some electrical connection. In such cases, the PCB 116 and the processing circuitry may access signal values from the EGS 100 and perform the processing remotely.

In one of the exemplary embodiments, the sensor assembly includes a first sensor cover positioned on a first end of the sensor assembly and a second sensor cover positioned on a second end of the sensor assembly. The first sensor cover defines a first capillary and the second sensor cover defines a second capillary. The sensor assembly further includes a first sensing unit, a second sensing unit, and a filter. The first sensing unit and the second sensing unit are positioned between the first sensor cover and the second sensor cover. Further, the filter is positioned on the second capillary. The filter, being reactive to a target gas, is configured to prevent an inflow of the target gas through the second capillary. Further, the first capillary is configured to allow the inflow of the target gas into the sensor assembly.

In one of the exemplary embodiments, the first sensing unit includes a sensing electrode, a reference electrode, and a counter electrode. The sensing electrode can be positioned on the first end of the sensor assembly. The second sensing unit includes an auxiliary electrode positioned on the second end of the sensor assembly. The reference electrode and the counter electrode are positioned between the sensing electrode and the auxiliary electrode.

Further, in accordance with some example embodiments, the sensor assembly further includes a printed circuit board (PCB) coupled to the sensor assembly. The printed circuit board is configured to determine a first current based on a first reaction between the target gas and the first sensing unit in the presence of at least one environmental parameter and to determine a second current based on a second reaction at the second sensing unit.

Further, in accordance with some example embodiments, the first current corresponds to an amount of the target gas at the first sensing unit and the second current corresponds to a magnitude of the at least one environmental parameter.

In some embodiments, the EGS can include a laminated capillary which acts as a filter when coupled with the auxiliary electrode. The laminated capillary can be operable to prevent the passage of the target gas therethrough.

In accordance with some example embodiments described herein, 'an electrochemical gas sensor (EGS) as described herein may correspond to a carbon monoxide sensor. In some embodiments, for example when the EGS is the carbon monoxide sensor, carbon monoxide (CO) may be reduced at the sensing electrode according to the following half reactions:

At the sensing electrode: CO+H2O→☐CO2+2H++2e− (Eq. 1)

At the counter electrode: 2H++½O2+2e−☐→☐H2O (Eq. 2)

Cell reaction: CO+½O2→☐CO2

In this aspect, an overall reaction inside the sensor may result in the consumption of carbon monoxide. In other embodiments, other gases may be consumed and generated according to other half reactions to achieve a substantially balanced redox reaction similar to but different from that described herein with regard to the example of the carbon monoxide sensor. In some embodiments, the overall reaction can optionally be maintained by means of a reference electrode and a potentiostat, the reference electrode and/or potentiostat being operable to lower a potential at the sensing electrode 216 and allow the reaction to proceed. The resulting current between the sensing electrode 216 and the counter electrode 222 may be proportional to the concentration of the ambient gas and, accordingly, a concentration of the target gas, e.g., carbon monoxide, can be thereby measured and/or monitored by the carbon monoxide sensor.

Further, in accordance with some example embodiments, the EGS 100 can be used in formaldehyde detection in home environment. A carbon cloth (i.e., a filter) can be positioned on the second capillary to keep formaldehyde away from the auxiliary electrode. The four-electrode sensor gives two current signals: a first current at the sensing electrode $I_{sens}$, and a second current at the auxiliary electrode $I_{aux}$. $I_{sens}$ can be comprised of baseline current $I_{base}$ and a response current $I_{resp}$ from electrochemical reaction of target gas, while second current $I_{aux}$ can be the current only from the baseline. The response current $I_{resp}$ (also known as differential current) is due to change in environmental parameters and thus the change in the target gas concentration by using the following relations:

Isens=Ibase+Iresp,

Iaux=Ibase

So, Iresp=Isens−Iaux.

According to some example embodiments described herein, a first dimension of the first capillary can be the same as a second dimension of the second capillary.

In some example embodiments, certain operations herein may be modified or further amplified as described below. Moreover, in some embodiments, additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art, the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The hardware used to implement the various illustrative logics, logical blocks, modules, and circuits described in connection with the aspects disclosed herein may include a general purpose processor, a digital signal processor (DSP), a special-purpose processor such as an application specific integrated circuit (ASIC) or a field programmable gate array (FPGA), a programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, or in addition, some steps or methods may be performed by circuitry that is specific to a given function.

In one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor-readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

The invention claimed is:

1. A sensor assembly, comprising:
a first sensor cover disposed on a first end of the sensor assembly, the first sensor cover defining a first capillary therethrough;
a second sensor cover disposed on a second end of the sensor assembly, the second sensor cover defining a second capillary therethrough;
a first sensing unit comprising a sensing electrode disposed on the first end of the sensor assembly;
a second sensing unit comprising an auxiliary electrode disposed on the second end of the sensor assembly, wherein each of the sensing electrode and the auxiliary electrode is positioned between the first sensor cover and the second sensor cover; and
a filter, disposed on the second capillary and defined by a material reactive to a target gas, wherein the filter is configured to prevent an inflow of the target gas through the second capillary.

2. The sensor assembly of claim 1, wherein the first sensing unit further comprises:
a reference electrode; and
a counter electrode,
wherein the reference electrode and the counter electrode are positioned between the sensing electrode and the auxiliary electrode.

3. The sensor assembly of claim 1, wherein the filter includes at least one of a membrane, a chemical substance, or a mixture of the chemical substance with glass fiber.

4. The sensor assembly of claim 3, wherein the membrane comprises an activated carbon filter.

5. The sensor assembly of claim 3, wherein the chemical substance includes potassium permanganate to absorb volatile organic compounds (VOC) and content of formaldehyde present in the target gas.

6. The sensor assembly of claim 1, further comprising a printed circuit board (PCB) coupled to the sensor assembly, the printed circuit board configured to:
determine a first current based on a first reaction between the target gas and the first sensing unit in the presence of at least one environmental parameter; and
determine a second current based on a second reaction at the second sensing unit.

7. The sensor assembly of claim 6, wherein the first current corresponds to an amount of the target gas at the first sensing unit and the second current corresponds to a magnitude of the at least one environmental parameter.

8. The sensor assembly of claim 7, wherein the printed circuit board is further configured to determine a differential current based on the first current and the second current, wherein the differential current corresponds to an amount of noise level based on the magnitude of the at least one environmental parameter.

9. The sensor assembly of claim 6, wherein the at least one environmental parameter includes at least one of a temperature value or a humidity value, within the sensor assembly.

10. The sensor assembly of claim 1, wherein the first capillary is configured to allow the inflow of the target gas into the sensor assembly.

11. A sensor assembly, comprising:
a first sensing unit comprising a sensing electrode;
a second sensing unit comprising an auxiliary electrode;
a first sensor cover disposed on the auxiliary electrode, the first sensor cover defining a first capillary;
wherein the first capillary is laminated with a chemical substance, reactive to a target gas, to prevent an inflow of the target gas through the first capillary; and
a second sensor cover disposed on the sensing electrode, the second sensor cover defining a second capillary and permitting the inflow of the target gas therethrough.

12. The sensor assembly of claim 11, wherein the first sensing unit further comprises a reference electrode and a counter electrode, and wherein the reference electrode and the counter electrode are positioned between the sensing electrode and the auxiliary electrode.

13. The sensor assembly of claim 11, wherein the second sensing unit is disposed on a first end of the sensor assembly and the first sensing unit is disposed on a second end of the sensor assembly.

14. The sensor assembly of claim 11, wherein the chemical substance includes at least one of potassium permanganate, or a mixture of glass fiber with potassium permanganate.

15. A sensor assembly, comprising:
a housing comprising:
a first sensor cover, disposed on a first end of the housing, the first sensor cover defining a first capillary which is configured to allow a target gas to pass therethrough;
a second sensor cover, disposed on a second end of the housing, the second sensor cover defining a second capillary;
a first sensing unit;
a second sensing unit, wherein each of the first sensing unit and the second sensing unit is positioned between the first sensor cover and the second sensor cover; and
a filter, defined by a material reactive to the target gas, positioned to be in fluidic communication with the second capillary, the filter configured to prevent an inflow of the target gas therethrough.

16. The sensor assembly of claim 15, wherein the first sensing unit comprises:
   a sensing electrode coupled with the first capillary;
   a reference electrode; and
   a counter electrode, and
   wherein the second sensing unit comprises an auxiliary electrode coupled with the second capillary within the housing, and wherein the reference electrode and the counter electrode are positioned between the sensing electrode and the auxiliary electrode.

17. The sensor assembly of claim 15, wherein the filter includes at least one of a membrane, a chemical substance, and a mixture of chemical substance with glass fiber.

18. The sensor assembly of claim 15, further comprising a printed circuit board configured to:
   determine a first current based on a first reaction, in the presence of at least one environmental parameter, and
   determine a second current based on a second reaction at the second sensing unit.

19. The sensor assembly of claim 18, wherein the first current corresponds to an amount of the target gas at the first sensing unit and the second current corresponds to a magnitude of the at least one environmental parameter at the second sensing unit.

20. The sensor assembly of claim 18, wherein the printed circuit board is further configured to determine a differential current based on the first current and the second current, wherein the differential current corresponds to an amount of noise level based on the magnitude of the at least one environmental parameter.

* * * * *